United States Patent [19]

Cushing

[11] Patent Number: 4,549,612
[45] Date of Patent: Oct. 29, 1985

[54] SOIL SAMPLER
[75] Inventor: Nelson N. Cushing, Glendale, Ariz.
[73] Assignee: Theresa Caldwell, Peoria, Ariz.
[21] Appl. No.: 565,719
[22] Filed: Dec. 27, 1983
[51] Int. Cl.$^4$ ............................................. E21B 25/00
[52] U.S. Cl. ........................................ 175/20; 175/58; 73/864.44
[58] Field of Search .......................... 175/20, 58, 321; 166/240; 47/48.5; 111/92, 96; 172/22; 73/864.44, 864.45

[56] References Cited

U.S. PATENT DOCUMENTS

| | | | |
|---|---|---|---|
| 1,162,901 | 12/1915 | Cantey | 73/864.44 |
| 2,283,650 | 5/1942 | Sanborn | 175/20 |
| 3,236,531 | 2/1966 | McConnell | 166/240 |
| 3,326,049 | 6/1967 | Eley | 73/864.44 |
| 3,464,732 | 9/1969 | Woodward | 172/22 |

FOREIGN PATENT DOCUMENTS

| | | | |
|---|---|---|---|
| 202491 | 3/1966 | Sweden | 175/20 |
| 289333 | 11/1973 | U.S.S.R. | 175/20 |

*Primary Examiner*—Stephen J. Novosad
*Assistant Examiner*—William P. Neuder
*Attorney, Agent, or Firm*—Jordan M. Meschkow

[57] ABSTRACT

An apparatus for removing soil samples from the root zone of a potted plant includes a first longitudinal tubular member and a second longitudinal member telescopically mounted within the first tubular member. The second member has a lower blunt end which protrudes slightly beyond the lower beveled end of the outer tubular member such that when the apparatus is caused to penetrate the root system of a plant, the roots are not damaged or severed. Having reached a desired depth, the center member may be extracted a predetermined distance such that further penetration of the apparatus will result in soil being deposited in the cylinderical opening at the bottom of said outer tubular member. The outer tubular member may be graduated so as to give a visual indication of its depth of penetration. Furthermore, means may be provided for locking the central member in its extracted position and in its penetration position.

10 Claims, 14 Drawing Figures

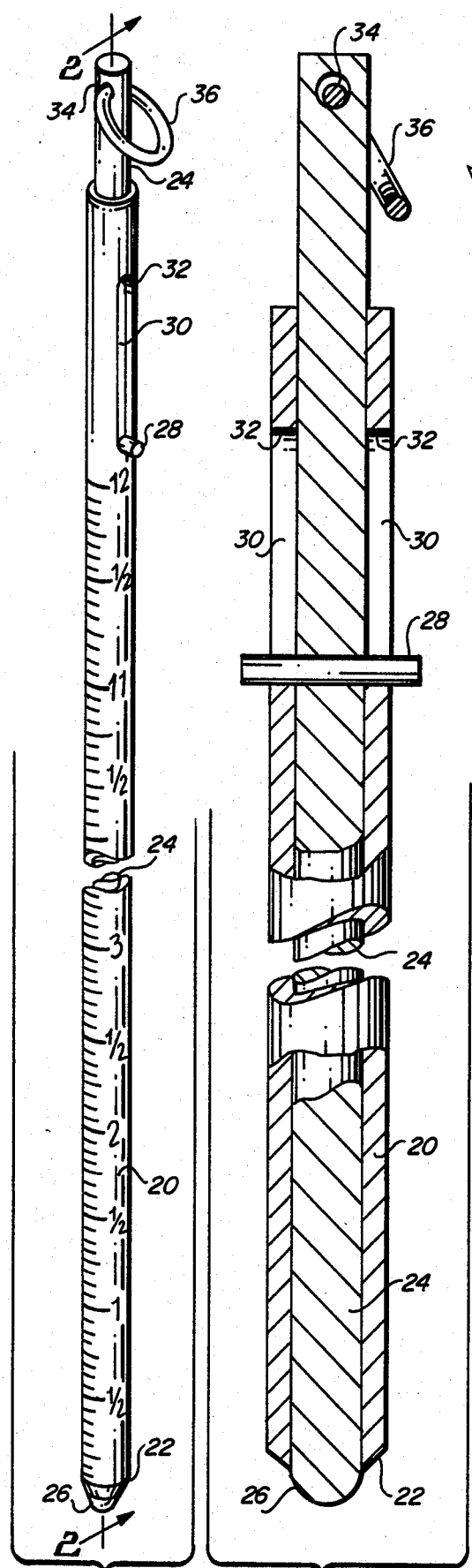
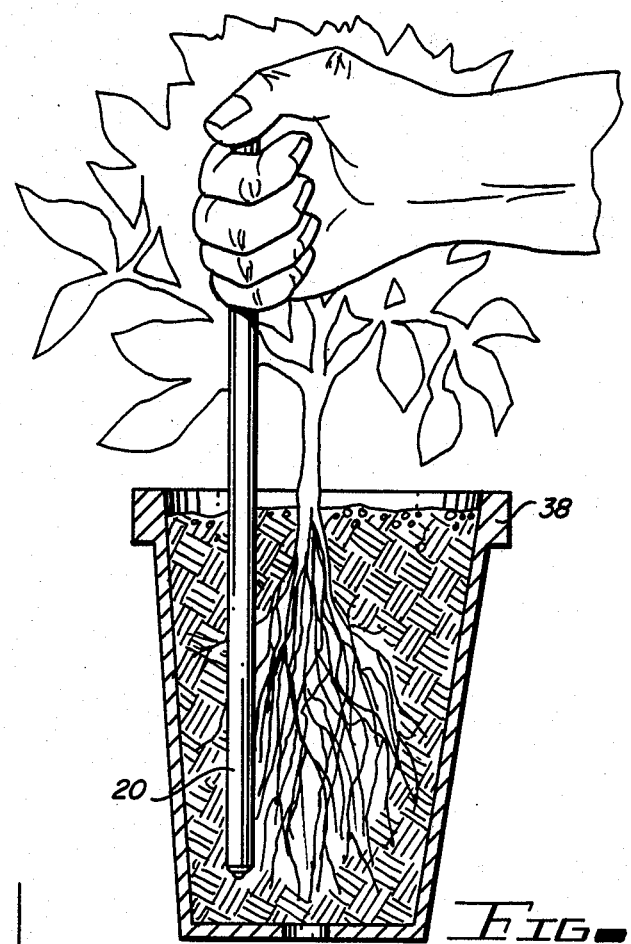
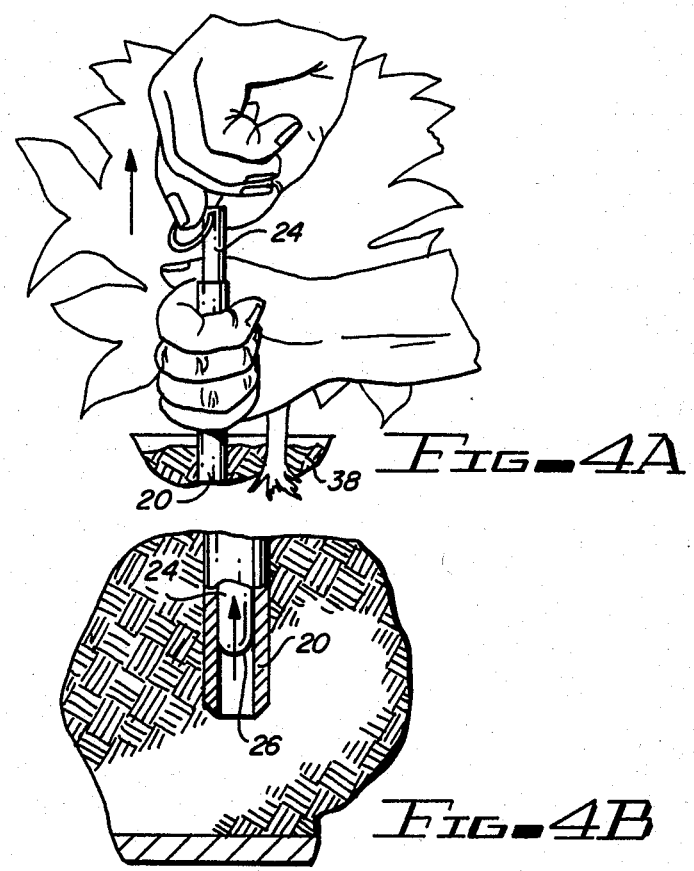
FIG.-1  FIG.-2  FIG.-3  FIG.-4A  FIG.-4B

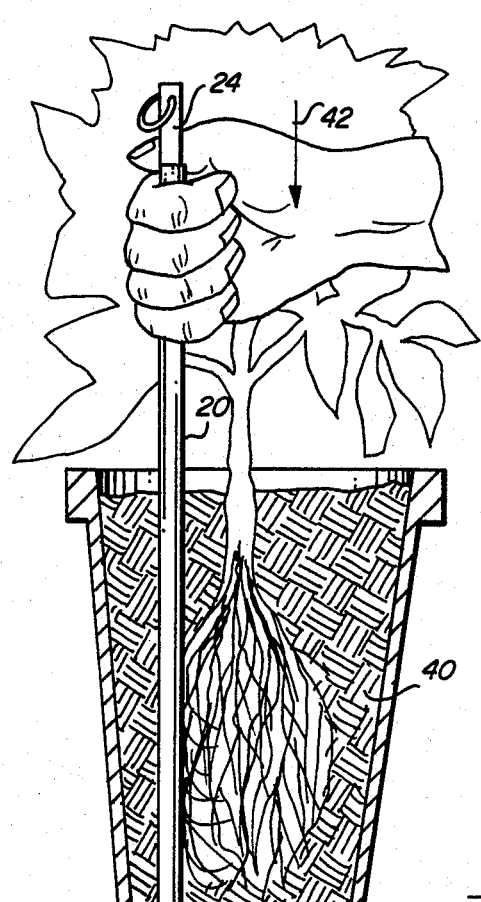
FIG-5A
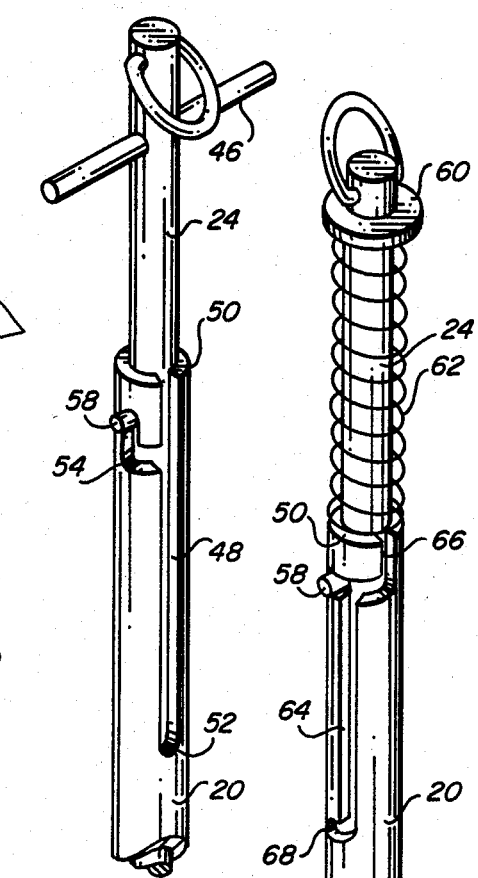
FIG-7
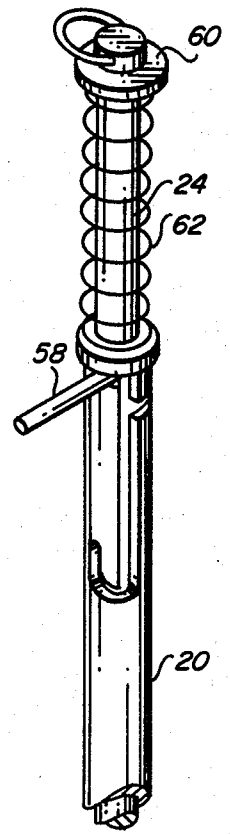
FIG-9  FIG-11
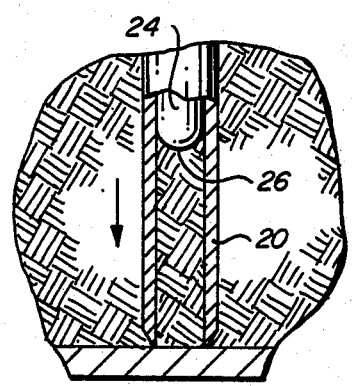
FIG-5B
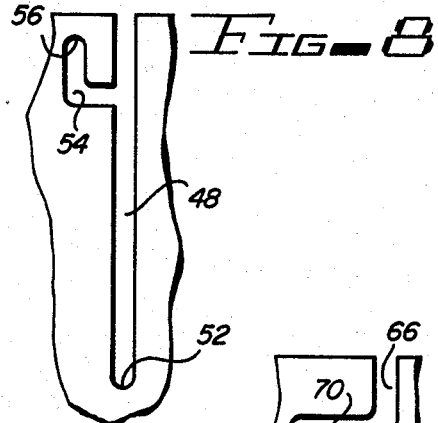
FIG-8
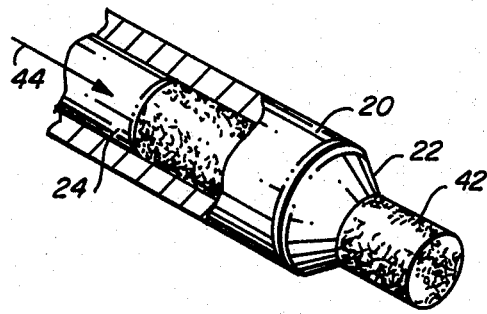
FIG-6
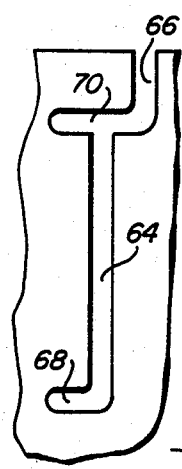
FIG-12
FIG-10

SOIL SAMPLER

BACKGROUND OF THE INVENTION

This invention relates generally to an apparatus for sampling soil to determine its moisture content and, more particularily, to an apparatus for retrieving soil samples from the root zone of a potted plant or the like in order to determine if watering is necessary.

Prior Art

There are many reasons for removing samples of soil or earth and the prior art is replete with devices for accomplishing same. For example, U.S. Pat. No. 1,109,446, issued Sept. 1, 1914 and entitled Soil Tester, describes a device consisting essentially of a cylinderical body tube which is tapered at its lower end and carried thereat a sharpened mouth piece which may be bored into the ground so that a cylinderical filler of earth will be projected upwardly into the body tube and into a glass tube or magazine which is removably placed in the body tube. In this case, the soil may be hermetically sealed and placed in storage until such time as it is convenient to analyze the soil.

U.S. Pat. No. 3,273,930, issued Sept. 20, 1966 and entitled Soil-Extracting Implements, describes an apparatus for extracting and replacing soil at points where flower bulbs are to be planted comprising a long tube positioned vertically when in use and having teeth at its lower end for cutting into the soil to form a hole in which the bulb is planted.

U.S. Pat. No. 3,326,049, issued June 20, 1967 and entitled Soil Sampling Device, relates to an apparatus for determining the volume of samples of soil which includes an uninterrupted cylinderical body which has a lower outer edge which is beveled so as to provide a sharp circular edge to facilitate insertion into the soil to be sampled.

U.S. Pat. No. 3,707,197, issued Dec. 26, 1972 and entitled Ground Core Removing Tool, describes a manual ground core cutting, extracting and replacing tool for use by, for example, collectors of burried metal coins, objects and artifacts. The device includes a vertically elongated cylinder having a handle means at its upper end and having a lower open end which is provided with an annular cutting edge.

It is also well known, that in the case of household depotted plants and the like, it would be most desirable to have a convenient means of determining whether there is sufficient moisture in the root zone of the plant. This could be accomplished by removing a sample of the soil near the bottom of the pot (i.e. in the root zone of the plant) to determine its moisture content. Unfortunately, none of the known soil sampling devices described above are suitable for this purpose for the following reasons. First, in each case, the devices remove a sample of soil which extends from the surface to a point below the surface. The devices are not capable of simply removing a small sample of soil from the plant's root zone. Secondly, each of the known devices includes a cutting mechanism at its lower end to facilitate insertion of the tool into the soil. In the case of a potted plant, however, such a cutting mechanism would damage the plant's roots.

SUMMARY OF THE INVENTION

It is an object of the present invention to provide an improved soil sampling apparatus.

It is a further object of the present invention to provide an improved apparatus for determining the necessity of watering household potted plants and the like.

It is a still further object of the present invention to provide an apparatus for removing samples of soil from below the surface without removing surface soil.

Yet another object of the present invention is to provide an apparatus for removing small samples of soil from the root zone of a potted plant.

Yet another object of the present invention is to provide an apparatus for removing small samples of soil from the root zone of a potted plant including means for measuring the depth at which sampling is desired.

A still further object of the present invention is to provide an apparatus for removing small samples of soil from the root zone of a potted plant without damaging the plants root system.

Another object of the present invention is to provide an apparatus for removing small samples of soil from the root zone of a potted plant which is simple and easy to use.

It is a still further object of the present invention to provide an apparatus for removing small samples of soil from the root zone of a potted plant which is sturdy and inexpensive to manufacture.

According to a broad aspect of the invention there is provided an apparatus for removing soil samples from the root zone of a potted plant, or the like, comprising a first longitudinal tubular member having upper and lower ends. A second longitudinal mounted member is telescopically mounted within the first tubular member and has a blunt lower end which protrudes slightly beyond the lower end of the tubular member when the apparatus is being caused to penetrate the potted plant's root system. Having passed through the root system, means are provided for extracting the inner second longitudinal member so as to cause the blunt end to be raised upward within the first longitudinal tubular member by a predetermined distance such that further penetration of the sampling apparatus will result in soil being deposited within the lower end of the first longitudinal tubular member. The outer tubular member may be calibrated so as to enable a user to determine to what distance the apparatus must penetrate the soil in order to clear the root system at which point the inner telescopic member is raised. Various mechanisms are described for fixing the relative positions of said inner telescopic member and said outer tubular member during both the penetration mode and the sampling mode.

The above, and other objects, features and advantages of the present invention will be more clearly understood from the following detailed description taken in conjunction with the accompanying drawings in which:

BRIEF DESCRIPTION OF THE DRAWINGS

FIG. 1 illustrates a first embodiment of the inventive soil sampling apparatus;

FIG. 2 is a cross sectional view of the apparatus shown in FIG. 1 taken along line 2—2;

FIGS. 3, 4A, 4B, 5A, 5B and 6 illustrate various stages in the use of the apparatus shown in FIG. 1 to extract a soil sample from the root zone of a potted plant;

FIGS. 7 and 8 illustrate a first mechanism for fixing the position of the telescopic center member relative to the outer tubular member;

FIGS. 9 and 10 illustrate a second mechanism for fixing the positional relationship between the inner and outer members; and FIGS. 11 and 12 illustrate yet another embodiment of a mechanism for fixing the positional relationship between the inner and outer members.

DESCRIPTION OF THE PREFERRED EMBODIMENT

Referring to FIGS. 1 and 2, the inventive soil sampling apparatus comprises an outer tubular member 20 having a lower beveled edge 22 and an inner member or rod 24 telescopically mounted within tubular member 20 and having a blunt lower end 26. A pin or rod 28 is fixedly coupled to central member 24 and extends through slots 30 in tubular member 20. Thus, slots 30 limit the movement of center rod 24 between a penetration position wherein blunt end 26 protrudes slightly beyond beveled edge 22 (shown in FIGS. 1 and 2) and a sampling position wherein center rod 24 is extracted or moved upward within tubular member 20 such that pin 28 abuts the upper end 32 of slots 30. For reasons which will become apparent, outer tubular member 20 may exhibit a graduated scale such as is shown in FIG. 1 in English or metric units which will, during use of the apparatus, give an indication of its depth of its penetration into the soil of a potted plant. To facilitate handling and storage, a ring 26 may be provided through aperture 34 at the upper end of telescopic rod 24. Both outer tubular member 20 and inner telescopic member 24 may be made of a variety of non-corrosive materials such as aluminum, steel, plastic, etc.

The inventive soil sampling apparatus is utilized by first manually adjusting the relative positions of outer tubular member 20 and inner rod 24 such that pin 28 abuts the lower edge of slot 30 so as to cause blunt end 26 to protrude slightly from beveled edge 22. In this configuration, the apparatus is manually caused to penetrate the soil and root zone of a potted plant 38 as is shown in FIG. 5. With blunt end 26 protruding slightly from beveled edge 22, damage to any of the plant's roots, or the cutting thereof, is avoided.

Prior to penetration, it would be desirable to have some idea of how deep the apparatus must penetrate to reach a region where sampling is desired. This may be simply accomplished by first placing the apparatus in its penetration mode exterior of but adjacent to potted plant 38 and noting the depth on the graduated scale on outer tubular member 20. The apparatus may then be closed to penetrate the soil and root zone until the previously noted depth is achieved. This situation is shown in FIG. 3.

Once the desired depth is achieved, center rod 24 is pulled upward or extracted manually until pin 28 abuts the upper terminus of slots 30 closing blunt end 26 to recede into tubular member 20 as is shown in FIGS. 4A and 4B.

The apparatus is now in the sampling mode and is manually caused to further penetrate the soil 40 by manually applying a downward pressure as indicated by arrow 42 in FIG. 5A while maintaining center rod 24 in its retracted position relative to outer tubular member 20. This additional penetration in the sampling mode causes soil to be deposited within the cylinderical cavity extending between beveled edge 22 of tubular member 20 and blunt end 26 of center rod 24 as is shown in FIG. 5B.

The entire device is next extracted from the soil and the soil sample 42 ejected by manually moving center rod 24 in the direction of arrow 44 (i.e. back to the penetration position) as is shown in FIG. 6.

FIGS. 7 and 8 illustrate an ultimate embodiment of the present invention wherein center rod 24 is provided with a T-type handle 46 to assist in manually adjusting the relative of outer tubular member 20 and inner telescopic rod 24. Additionally, instead of slots 30, shown in FIGS. 1 and 2 to limit the movement of rod 24, a slot 48 is provided in tubular member 20 which extends from the upper edge 50 of tubular member 20 to a lower terminus 52. A secondary right angle slot 54 has a horizontal portion which joins slot 48 and a vertical portion having an upper terminus 56. A pin 58 is fixedly coupled to center rod 24 and is capable of sliding movement within slots 48 and 54. Thus, manipulating rod 24 and therefore pin 58 such that pin 58 abuts lower terminus 52 of slot 48, the soil sampling apparatus is in the penetration mode. By manipulating rod 24 and therefore 58 until pin 58 abuts terminus 56 of slot 54, center rod 24 is locked into a sampling mode such as is shown in FIG. 7. In this mode, rod 24 need not be manually held in position relative to outer tubular member 20 when the apparatus is being depressed into the soil to cause soil to be deposited within the lower end of tubular member 20. Furthermore, rod 24 may be entirely removed from outer tubular member 20 by simply maneuvering pin 58 through slot 48 and past the upper edge 50 of tubular member 20.

Referring to FIGS. 9 and 10, an ultimate embodiment is shown wherein a flange 60 is coupled proximate the upper end of center rod 24, and a coil spring 62 is restrained between flange 60 and upper edge 50 of tubular member 20. In this case, the slot arrangement in outer tubular member 20 includes a first vertical portion 64, a second vertical portion 66, a first transverse portion 68 and a second transverse portion 70. In this case, rod 24 may be removed from tubular member 20 by negotiating pin 58 through vertical slot portions 64 and 60. Postioning pin 58 in transverse portion 68 locks rod 24 in the penetration position. In contrast, positioning pin 58 in transverse slot portion 70 locks rod 24 in the sampling position. Coil spring 62 merely biases rod 24 towards the sampling position.

The embodiment shown in FIGS. 11 and 12 is improved by extending the length of pin 58 so as to permit easy manipulation of the pin and therefore rod 24 relative outer tubular member 20. The slot itself consists of a first vertical portion 72, a second vertical portion 74, an L-shaped portion 76 having upper terminus 78, and a transverse portion 80. Again, rod 24 may be completely removed from tubular member 20 by negotiating pin 58 through vertical slot portions 72 and 74. By placing pin 58 at terminus 78, the apparatus is locked in the penetration mode. Of course, the vertical force being exerted on center rod 24 by spring 62 will assist in locking rod 24 in the penetration position. The apparatus may be locked in the sampling position by placing pin 58 in transverse slot portion 80.

The above description is given by way of example only. Changes in form and details may be made by one skilled in the art without departing from the scope of the invention as defined by the appended claims.

I claim:

1. An apparatus for removing soil samples from the root zone of a potted plant or the like, comprising:
   a first longitudinal tubular member having upper and lower ends;
   a second longitudinal member telescopically mounted within said first tubular member, said first tubular member, said second member having a blunt lower end which protrudes slightly beyond the lower end of said first tubular member when said apparatus penetrates through said root zone; and
   first means for extracting said second member to raise said blunt lower end within said first tubular member such that further penetration of said apparatus will result in soil being deposited within said lower end of said first tubular member, said first means comprising a slot in said first tubular member proximate its upper end, and a protrusion fixedly coupled to said second member proximate its upper end and extending into said slot to define the limit of movement of said second member in said first tubular member, said slot extending to the upper end of said first tubular member to permit complete removal of said second member from said first tubular member.

2. An apparatus according to claim 1 wherein said lower end of said first longitudinal tubular member is beveled.

3. An apparatus according to claim 1 wherein said first tubular member has indicia on an outer surface thereof to indicate its depth of penetration.

4. An apparatus according to claim 1 wherein said slot includes a first portion for locking said second member in its extracted position within said first tubular member.

5. An apparatus according to claim 4 wherein said slot includes a second portion for locking said second member in its penetration position within said first tubular member.

6. An apparatus according to claim 1 further comprising handle means fixedly coupled to said second member proximate its upper end.

7. An apparatus according to claim 1 further comprising spring means coupled to said first tubular member and said second member to bias its second member in its extracted position.

8. An apparatus according to claim 7 wherein said protrusion is a pin extending outward from said second member through said slot a sufficient distance to be manually controlled for repositioning said second member relative to said first tubular member.

9. An apparatus according to claim 8 wherein said spring means is a coil spring positioned between an upper end of said first tubular member and the upper end of said second member.

10. An apparatus according to claim 9 wherein said second member is a rod.

* * * * *